US006409770B1

(12) United States Patent
Weiss et al.

(10) Patent No.: US 6,409,770 B1
(45) **Date of Patent: *Jun. 25, 2002**

(54) BLEACHING AND WASHING AGENTS WITH ENZYME BLEACHING SYSTEM

(75) Inventors: Albrecht Weiss, Langenfeld; Maria Grothus, Friedberg; Achim Richert, Juelich, all of (DE)

(73) Assignee: Henkel Kommanditgesellschaft auf Aktien, Duesseldorf (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/142,244

(22) PCT Filed: Nov. 29, 1996

(86) PCT No.: PCT/EP96/05282

§ 371 (c)(1), (2), (4) Date: Dec. 11, 1998

(87) PCT Pub. No.: WO97/21796

PCT Pub. Date: Jun. 19, 1997

(30) Foreign Application Priority Data

Dec. 8, 1995 (DE) ........................................ 195 45 729

(51) Int. Cl.[7] ............................ D06L 3/02; C12N 9/04; C11D 3/386

(52) U.S. Cl. .................. 8/107; 8/137; 8/139; 435/190; 510/375; 510/376; 510/439; 510/530; 510/297; 510/392

(58) Field of Search ................................ 510/375, 376, 510/439, 530, 297, 392; 8/107, 137, 139; 435/190

(56) References Cited

U.S. PATENT DOCUMENTS

| | | | | |
|---|---|---|---|---|
| 3,635,828 A | | 1/1972 | Benjamin et al. | 252/99 |
| 3,784,476 A | | 1/1974 | van Kampen et al. | 252/109 |
| 4,356,099 A | * | 10/1982 | Davies et al. | 252/90 |
| 4,585,642 A | | 4/1986 | Rieck | 423/333 |
| 4,664,839 A | | 5/1987 | Rieck | 252/175 |
| 4,820,439 A | | 4/1989 | Rieck | 252/135 |
| 4,889,644 A | | 12/1989 | Amberg et al. | 252/8.9 |
| 5,183,651 A | | 2/1993 | Schimmel et al. | 423/334 |
| 5,200,236 A | * | 4/1993 | Lang et al. | 427/213 |
| 5,229,095 A | | 7/1993 | Schimmel et al. | 423/334 |
| 5,230,822 A | * | 7/1993 | Kamel et al. | 252/174.13 |
| 5,236,682 A | | 8/1993 | Schimmel et al. | 423/334 |
| 5,258,132 A | * | 11/1993 | Kamel et al. | 252/94 |
| 5,268,156 A | | 12/1993 | Schimmel et al. | 423/334 |
| 5,308,596 A | | 5/1994 | Kotzian et al. | 423/333 |
| 5,318,733 A | | 6/1994 | Carduck et al. | 264/15 |
| 5,356,607 A | | 10/1994 | Just | 423/334 |
| 5,382,377 A | | 1/1995 | Raehse et al. | 252/174 |
| 5,417,951 A | | 5/1995 | Just | 423/334 |
| 5,445,651 A | * | 8/1995 | Thoen et al. | 8/111 |
| 5,474,576 A | * | 12/1995 | Thoen et al. | 8/111 |
| 5,494,488 A | | 2/1996 | Arnoldi et al. | 8/137 |
| 5,541,316 A | | 7/1996 | Engelskirchen et al. | 510/471 |
| 5,580,941 A | | 12/1996 | Krause et al. | 527/300 |
| 5,670,468 A | * | 9/1997 | Moens | 510/226 |

FOREIGN PATENT DOCUMENTS

| | | |
|---|---|---|
| AU | 94 58592 | 8/1994 |
| CA | 1 036 455 | 8/1978 |
| DE | 16 17 232 | 2/1971 |
| DE | 20 64 146 | 7/1971 |
| DE | 20 32 768 | 1/1972 |
| DE | 24 12 837 | 10/1974 |
| DE | 25 57 623 | 6/1977 |
| DE | 40 41 752 | 6/1992 |
| DE | 42 21 381 | 2/1994 |
| DE | 42 31 767 | 3/1994 |
| DE | 43 00 772 | 7/1994 |
| DE | 43 03 320 | 8/1994 |
| DE | 44 16 438 | 11/1995 |
| DE | 44 17 734 | 11/1995 |
| DE | 44 22 433 | 1/1996 |
| DE | 44 22 609 | 1/1996 |
| DE | 44 43 177 | 6/1996 |
| DE | 195 29 905 | 2/1997 |
| DE | 195 36 082 | 4/1997 |
| DE | 196 05 688 | 8/1997 |
| DE | 196 13 103 | 10/1997 |
| DE | 196 20 411 | 10/1997 |
| DE | 196 20 267 | 11/1997 |
| EP | 0 072 098 | 2/1983 |
| EP | 0 164 514 | 12/1985 |
| EP | 0 164 552 | 12/1985 |
| EP | 0 168 526 | 1/1986 |
| EP | 0 170 360 | 2/1986 |
| EP | 0 270 608 | 6/1988 |
| EP | 0 272 030 | 6/1988 |
| EP | 0 294 753 | 12/1988 |
| EP | 0 295 525 | 12/1988 |

(List continued on next page.)

OTHER PUBLICATIONS

Derwent Patent Abstract (WPAT) 95–175511/23.
Derwent Patent Abstract (WPAT) 94–127130/16.
Derwent Patent Abstract (WPAT) 71–45401S/27.

(List continued on next page.)

*Primary Examiner*—Yogendra N. Gupta
*Assistant Examiner*—Brian P. Mruk
(74) *Attorney, Agent, or Firm*—Stephen D. Harper; Glenn E.J. Murphy

(57) ABSTRACT

A bleaching detergent composition comprising an enzyme having amino alcohol oxidase activity, a substrate for said enzyme, and a bleach catalyst or activator, a method of bleaching fabric stains with an enzymatic bleaching system comprising an enzyme having amino alcohol oxidase activity and a substrate for said enzyme, and a method of reducing dye transfer in a wash liquor by providing the liquor with an effective amount of an enzymatic bleaching system comprising an enzyme having amino alcohol oxidase activity and a substrate for said enzyme.

11 Claims, No Drawings

FOREIGN PATENT DOCUMENTS

| | | | | |
|---|---|---|---|---|
| EP | 0 304 331 | | | 2/1989 |
| EP | 0 392 592 | | | 10/1990 |
| EP | 0 423 890 | | | 4/1991 |
| EP | 0 425 427 | | | 5/1991 |
| EP | 0 425 428 | | | 5/1991 |
| EP | 0 436 835 | | | 7/1991 |
| EP | 0 443 651 | | | 8/1991 |
| EP | 0 446 982 | | | 9/1991 |
| EP | 0 453 003 | | | 10/1991 |
| EP | 0 458 397 | | | 11/1991 |
| EP | 0 458 398 | | | 11/1991 |
| EP | 0 486 592 | | | 5/1992 |
| EP | 0 502 325 | | | 9/1992 |
| EP | 538228 | A1 | * | 4/1993 |
| EP | 0 544 490 | | | 6/1993 |
| EP | 0 544 519 | | | 6/1993 |
| EP | 0 548 599 | | | 6/1993 |
| EP | 0 549 271 | | | 6/1993 |
| EP | 0 549 272 | | | 6/1993 |
| EP | 0 603 931 | | | 6/1994 |
| EP | WO 95/17496 | | * | 6/1995 |
| EP | 0 693 550 | | | 1/1996 |
| JP | 04 238 809 | | | 8/1992 |
| JP | 04 260 610 | | | 9/1992 |
| JP | 7097597 | A | * | 4/1995 |
| WO | WO89/09813 | | | 10/1989 |
| WO | WO90/09428 | | | 8/1990 |
| WO | WO90/09440 | | | 8/1990 |
| WO | WO91/08171 | | | 6/1991 |
| WO | WO92/11347 | | | 7/1992 |
| WO | WO93/15176 | | | 8/1993 |
| WO | WO93/16110 | | | 8/1993 |
| WO | WO94/23005 | | | 10/1994 |
| WO | WO94/25574 | | | 11/1994 |
| WO | WO 94/25574 | | * | 11/1994 |
| WO | WO95/07972 | | | 3/1995 |
| WO | WO95/27775 | | | 10/1995 |

OTHER PUBLICATIONS

Derwent Patent Abstract (WPAT) 77–47181Y/27.
Derwent Patent Abstract (WPAT) 70–06036R/05.
Derwent Patent Abstract (WPAT) 72–03876T/03.
Derwent Patent Abstract (WPAT) 92–218091/27.
Derwent Patent Abstract (WPAT) 85–147286/25.
Derwent Patent Abstract (WPAT) 96–050463/06.
Derwent Patent Abstract (WPAT) 96–050519/06.
Derwent Patent Abstract (WPAT) 88–362045/51.
Derwent Patent Abstract (WPAT) 96–287166/29.
Derwent Patent Abstract (WPAT) 97–133790/13.
Derwent Patent Abstract (WPAT) 98–019669/03.
Derwent Patent Abstract (WPAT) 97–204334/19.
Derwent Patent Abstract (WPAT) 97–416938/39.
Derwent Patent Abstract (WPAT) 97–481969/45.
Derwent Patent Abstract (WPAT) 96–011551/02.
Derwent Patent Abstract (WPAT) 97–481903/45.
Derwent Patent Abstract (WPAT) 93–259656/33.
Derwent Patent Abstract (WPAT) 94–035002/04.
Derwent Patent Abstract (WPAT) 94–235530/29.
Derwent Patent Abstract (WPAT) 94–280420/35.
Derwent Patent Abstract (WPAT) 96–000404/01.
Derwent Patent Abstract (WPAT) 74–75753V/44.
Derwent Patent Abstract (WPAT) 91–126877/18.
Derwent Patent Abstract (WPAT) 85–270605/44.
Derwent Patent Abstract (WPAT) 91–172613/24.
Derwent Patent Abstract (WPAT) 92–335303/41.
Derwent Patent Abstract (WPAT) 92–360500/44.
Derwent Patent Abstract (WPAT) 93–206465/26.
Derwent Patent Abstract (WPAT) 92–301673/37.
Derwent Patent Abstract (WPAT) 91–126878/18.
Derwent Patent Abstract (WPAT) 91–209554/29.
Derwent Patent Abstract (WPAT) 85–290431/47.
Derwent Patent Abstract (WPAT) 88–355215/50.
Derwent Patent Abstract (WPAT) 92–218091/27.
Derwent Patent Abstract (WPAT) 94–31135/39.
Derwent Patent Abstract (WPAT) 91–073523/10.

* cited by examiner

BLEACHING AND WASHING AGENTS WITH ENZYME BLEACHING SYSTEM

BACKGROUND OF THE INVENTION

This invention relates to a bleach or detergent which, besides typical ingredients, contains a bleaching system of an amino alcohol oxidase or D-amino acid oxidase and a substrate for this oxidase.

Modern heavy-duty detergents and bleaching washing aids, so-called bleaches, normally contain an oxygen-based oxidizing agent, more particularly a peracid, a peracid salt, hydrogen peroxide or a substance which yields hydrogen peroxide under aqueous in-use conditions. Since the bleaching effect of hydrogen peroxide on its own is often found to be inadequate, bleaching systems of a per compound which yields hydrogen peroxide in water and a bleach activator which generates a peracid under perhydrolysis conditions are generally used. The most prominent example of such a bleaching system is the widely used combination of alkali metal perborate and N,N,N',N'-tetraacetyl ethylenediamine. There has been no shortage of attempts to improve this bleaching system by modification. For example, it is proposed in International patent application WO 89/09813 to use a peroxidase enzyme, i.e. an enzyme which catalyzes the reaction of hydrogen peroxide with organic or inorganic substances, as bleach activator.

Besides inorganic hydrogen peroxide precursors such as, for example, perborate, percarbonate, perphosphate and persilicate, it has also occasionally been proposed to use enzymatic systems which are capable of producing hydrogen peroxide from oxygen, for example from atmospheric oxygen. Enzymes such as these are normally referred to as oxidases and are classified according to their substrate. Oxidases are redox enzymes with the classification EC 1 (classification of the Enzyme Commission) which are generally flavine-dependent and of which the oxidized form is capable of oxidizing a substrate. The resulting reduced form of the enzyme is reoxidized by molecular oxygen in aqueous systems, hydrogen peroxide being formed as another product. Examples of such enzymes and their substrates which follow the name of the enzyme are phenol oxidase, amino acid oxidase, xanthine oxidase, urate oxidase, alcohol oxidase, cholesterol oxidase and glucose oxidase.

DE-OS 19 18 729 describes detergents which, besides surfactants, contain 0.5% by weight to 10% by weight of glucose oxidase and 5% by weight to 30% by weight of glucose or starch. In the latter case, 0.5% by weight to 10% by weight of amyloglucosidase is said to be additionally present. DE-OS 20 64 146 discloses detergents containing 1% by weight to 50% by weight of water-soluble surfactant and 0.01% by weight to 2% by weight of lipoxidase. Polyunsaturated fatty acids are preferably present as substrates for the lipoxidase. DE-OS 25 57 623 describes detergents which, in addition to surfactants and builders, contain 0.3% by weight to 10% by weight of urate oxidase, galactose oxidase or $C_{1-3}$ alcohol oxidase and 3% by weight to 30% by weight of uric acid, galactose or $C_{1-3}$ alcohols and/or corresponding ketoalcohols. European patent EP 0 072 098 relates to liquid bleaches containing a $C_{1-4}$ alcohol oxidase and a $C_{1-4}$ alcohol. In European patent application EP 0 603 931, it is proposed to stabilize the glucose oxidase/glucose system in liquid detergents by the addition of $Cu^{2+}$ and/or $Ag^{+}$ ions and to enhance the bleaching effect of the enzymatically produced hydrogen peroxide by the presence of bleaching catalysts, more particularly metal porphines, metal porphyrines, metal phthalocyanines and/or haemine. The same objective is also followed by International patent application WO 95/07972 which describes bleaches containing an enzymatic system to produce hydrogen peroxide and a bleach-catalyzing coordination complex of Mn or Fe. International patent application WO 94/25574 discloses an L-amino acid oxidase of a certain strain of the microorganism *Trichoderma harzianum* and detergents containing this oxidase.

DESCRIPTION OF THE INVENTION

The problem addressed by the present invention was to provide a bleaching formulation with improved effectiveness of the enzymatically produced hydrogen peroxide under washing conditions.

It has now surprisingly been found that the bleaching effect of hydrogen peroxide produced enzymatically in typical washing, bleaching and cleaning liquors can be significantly increased, even in the absence of typical activators, if the hydrogen peroxide is produced in situ through the use of amino alcohol oxidase or D-amino acid oxidase.

Accordingly, the present invention relates to a bleach or detergent containing an enzymatic bleaching system which is capable of producing hydrogen peroxide under in-use conditions and, optionally, synthetic surfactant, organic and/or inorganic builder and other typical ingredients of bleaches or detergents, characterized in that the bleaching system consists of an enzyme having amino alcohol oxidase or D-amino acid oxidase activity and of a substrate for this enzyme.

The present invention also relates to the use of a bleaching system of an enzyme having amino alcohol oxidase or D-amino acid oxidase activity and of a substrate for this enzyme for bleaching fabric stains under washing conditions.

The present invention also relates to the use of a system of an enzyme having amino alcohol oxidase or D-amino acid oxidase activity and of a substrate for this enzyme for reducing dye transfer from dyed fabrics to undyed or differently colored fabrics when they come into contact under washing or rinsing conditions.

Amino alcohol oxidases catalyze the oxidation of primary alcohol functions of amino alcohols by oxygen to the corresponding acid function with formation of hydrogen peroxide. Where they are used, it is essential that an amino alcohol with a primary alcohol function be present as substrate for the amino alcohol oxidase. The preferred amino alcohol oxidase for the purposes of the present invention is choline oxidase (EC 1.1.3.17) which is used together with its substrate choline preferably present as halide. D-amino acid oxidases (EC 1.4.3.3) catalyze the reaction:

$$\text{D-amino acid}+H_2O+O_2\rightarrow\text{alpha-ketoacid}+NH_3+H_2O_2$$

According to the invention, preferred substrates for D-amino acid oxidases are—either individually or in the form of mixtures—glycine, D-alanine, D-arginine, D-asparagine, D-aspartic acid, D-cysteine, D-glutamine, D-glutamic acid, D-histidine, D-isoleucine, D-leucine, D-lysine, D-methionine, D-phenyl alanine, D-proline, D-serine, D-threonine, D-tryptophane, D-tyrosine and D-valine, which may be used without enantiomers or in admixture with their L-enantiomers. According to the invention, it is particularly preferred to use D-alanine.

The oxidases suitable for use in the bleaches/detergents according to the invention are enzymes obtainable from microorganisms or organs of higher animals which have an optimum pH preferably in the almost neutral to mildly alkaline range of about pH 6 to pH 9.5. The activity of enzymes is normally expressed in U/g, the unit 1 U corresponding to the activity of that quantity of enzyme which reacts 1 $\mu$mole of its substrate in 1 minute at pH 7/25° C. 1 U thus corresponds to 1/60 $\mu$catal. Choline oxidase as produced, for example, by alcaligenes species or by *Arthrobacter globiformis* is preferably used as the amino alcohol oxidase. D-amino acid oxidase of standardized activity, obtained for example from pig's kidneys, is commercially available and, like choline oxidase, can be obtained for example from the Sigma company. The oxidase is preferably used in the bleach/detergent according to the invention in such quantities that the bleaching composition/detergent as a whole has an oxidase activity of 30 U/g to 20,000 U/g and, more particularly, 60 U/g to 15,000 U/g. Bleaching systems/detergents with oxidase activities in the ranges mentioned release hydrogen peroxide sufficiently quickly for standard European machine washing processes. The enzymes with amino alcohol oxidase or D-amino acid oxidase activity used in accordance with the invention have a far higher activity than glucose oxidase under washing conditions.

The amount of substrate present for the oxidase in the bleach/detergent according to the invention is determined by the amount of hydrogen peroxide required to obtain the desired bleaching result. As a guide, it may be said that, in enzyme/substrate systems which release 1 mole of hydrogen peroxide for every mole of substrate reacted, the presence of about 0.05% by weight to 0.6% by weight of the substrate in the washing or bleaching liquor is generally sufficient to obtain a good bleaching result.

In contrast to the finding reported in WO 89/09813 that hydrogen peroxide has an increased bleaching effect on soiled textiles in the presence of enzymes which degrade this compound, applicants have found that the simultaneous presence of peroxidases or catalases and the bleaching system of an enzyme having oxidase activity and a substrate for this enzyme in the bleaches/detergents according to the invention is detrimental to the bleaching effect of the enzymatically produced hydrogen peroxide. Accordingly, if—for example for reasons of cost—it is intended to use enzyme preparations which, besides oxidase, also contain catalase and/or peroxidase (often isolated together with the oxidase from the producing microorganism), an inhibitor for these hydrogen-peroxide-destroying enzymes is preferably added to the bleach/detergent according to the invention. Hydroxylammonium salts in particular, for example hydroxylammonium sulfate, have been found to be extremely effective in this connection.

In principle, a bleach/detergent according to the invention may be formulated as required, for example as an aqueous or non-aqueous liquid bleach/detergent, a more or less viscous, aqueous or non-aqueous paste, a granular powder or in stick form or bar form, known processes of the relevant prior art being suitable for the production of such formulations. In one preferred embodiment, the bleach/detergent is present in the form of a free-flowing particulate product, for example as a powder, with a bulk density of 300 g/l to 1,200 g/l and, more particularly, in the range from 500 g/l to 900 g/l. In particulate products such as these, the oxidase is preferably adsorbed onto an inert support material, i.e. onto a support material which is not a substrate for the enzyme, encapsulated in shell-forming substances or used in the form of standard granules with inorganic and/or organic support materials. Enzyme granules such as these can be produced by processes known with other enzymes, as described for example in German patent 16 17 232, in German Offenlegungsschrifts 20 32 766 or 40 41 752 or in European patent applications EP 0 168 526, EP 0 170 360, EP 0 270 608 or EP 0 304 331. If other typical detergent enzymes, including in particular proteases, lipases, cutinases, amylases, pullulanases, hemicellulases and cellulases, are to be used in addition to oxidase, they may be accommodated in separate particles or may be used together with oxidase in the form of multi-enzyme granules as described, for example, in German patent applications DE 44 22 433 or DE 44 22 609 or in International patent applications WO 90/09440 or WO 90/09428 and in the prior-art literature cited therein.

With powder-form bleaches/detergents according to the invention and with non-aqueous liquid or paste-form bleaches/detergents, the oxidase substrate is not normally decomposed to any significant extent by the amino alcohol oxidase and/or D-amino acid oxidase in storage. In liquid or paste-form bleaches/detergents containing water, the enzymatic decomposition of the substrate in storage can become a problem, albeit one that can be solved by denying oxygen access to the bleach/detergent according to the invention. Accordingly, water-containing liquid or paste-form bleaches/detergents according to the invention, i.e. those containing more than about 3% by weight of water, are preferably stored in hermetically sealed packs from which they are only removed shortly before use. In the case of institutional machine washing processes, this can readily be done by the automatic dispensing of the detergent according to the invention from the transit container itself, as described for example in European patent EP 0 295 525. Liquid to paste-form bleaches/detergents according to the invention for use in domestic washing machines are preferably made up in portioned form, for example in bag form, the container material surrounding a detergent according to the invention, for example film-form polyvinyl alcohol, being selected so that it only dissolves under in-use conditions, i.e. in the washing machine itself during the washing process, and releases the detergent so that the bleaching system present in the detergent only then comes into contact with the oxygen present in the air and forms hydrogen peroxide.

In another embodiment of the bleach/detergent according to the invention similarly intended to increase stability in storage, the enzyme having oxidase activity and/or the substrate for this enzyme is encapsulated in a substance which is impermeable to the enzyme and/or its substrate at room temperature or in the absence of water, but which becomes permeable to the enzyme and/or its substrate under in-use conditions. Organic substances melting at temperatures above room temperature, more particularly at temperatures of 35° C. to 75° C., for example fatty alcohols, polyglycols, paraffin waxes or fatty acid esters, may be used for this purpose. Substances which do not melt under in-use conditions, but which are soluble or dispersible in water, for example fine-particle alkali metal alumosilicate, layer silicate, clay or bentonite, are also suitable.

The composition of the bleaches/detergents according to the invention may otherwise be selected virtually as required within the limits of known formulations. In particular, the bleaches/detergents according to the invention may contain builders, surfactants, water-miscible organic solvents, other enzymes, sequestering agents, electrolytes, pH regulators, additional peroxygen bleaching agents and other auxiliaries, such as optical brighteners, redeposition inhibitors, foam regulators, bleach activators, dyes and fragrances and, if desired, additional dye transfer inhibitors.

In addition to the bleaching system according to the invention, conventional bleach activators, i.e. compounds which form optionally substituted perbenzoic acid and/or aliphatic peroxocarboxylic acids containing 1 to 10 and, more particularly, 2 to 4 carbon atoms under perhydrolysis conditions, may be used. Conventional bleach activators which contain O- and/or N-acyl groups with the number of carbon atoms mentioned and/or optionally substituted benzoyl groups are suitable. Preferred bleach activators are polyacylated alkylene diamines, more particularly tetraacetyl ethylenediamine (TAED), acylated glycolurils, more particularly tetraacetyl glycoluril (TAGU), acylated triazine derivatives, more particularly 1,5-diacetyl-2,4-dioxohexahydro-1,3,5-triazine (DADHT), acylated phenol sulfonates, more particularly nonanoyl or isononanoyloxybenzene sulfonate, acylated polyhydric alcohols, more particularly triacetin, ethylene glycol diacetate and 2,5-diacetoxy-2,5-dihydrofuran and acetylated sorbitol and mannitol, and acylated sugar derivatives, more particularly pentaacetyl glucose (PAG), pentaacetyl fructose, tetraacetyl xylose and octaacetyl lactose, and acetylated, optionally N-alkylated glucamine and gluconolactone. The combinations of conventional bleach activators known from German patent application DE 44 43 177 may also be used. Bleach activators such as these are normally present in quantities of 1% by weight to 10% by weight and, more particularly, in quantities of 2% by weight to 5% by weight. In addition to or instead of the conventional bleach activators mentioned above, the sulfonimines and/or bleach-boosting transition metal salts or transition metal complexes known from European patents EP 0 446 982 and EP 0 453 003 may be present as so-called bleach catalysts. Suitable transition metal compounds include, in particular, the manganese-, iron-, cobalt-, ruthenium- or molybdenum-salen complexes known from German patent application DE 195 29 905 and the N-analog compounds thereof known from German patent application DE 196 20 267, the manganese-, iron-, cobalt-, ruthenium- or molybdenum-carbonyl complexes known from German patent application DE 195 36 082, the manganese, iron, cobalt, ruthenium, molybdenum, titanium, vanadium and copper complexes with nitrogen-containing tripod ligands described in German patent application DE 196 05 688, the cobalt-, iron-, copper- and ruthenium-ammine complexes known from German patent application DE 196 20 411, the manganese, copper and cobalt complexes described in German patent application DE 44 16 438, the cobalt complexes described in European patent application EP 0 272 030, the manganese complexes known from European patent application EP 0 693 550, the manganese, iron, cobalt and copper complexes known from European patent 0 392 592 and/or the manganese complexes described in European patent EP 0 443 651 or in European patent applications EP 0 458 397, EP 0 458 398, EP 0 549 271, EP 0 549 272, EP 0 544 490 and EP 0 544 519. Combinations of bleach activators and transition metal bleach catalysts are known, for example, from German patent application DE 196 13 103 and International patent application WO 95/27775. Bleach-boosting transition metal complexes, more particularly with the central atoms Mn, Fe, Co, Cu, Mo, V, Ti and/or Ru, are used in typical quantities, preferably in a quantity of up to 1% by weight, more preferably in a quantity of 0.0025% by weight to 0.25% by weight and most preferably in a quantity of 0.01% by weight to 0.1% by weight, based on the bleach/detergent as a whole.

The bleaches/detergents according to the invention may contain one or more surfactants, more particularly anionic surfactants, nonionic surfactants and mixtures thereof. Suitable nonionic surfactants are, in particular, alkyl glycosides and ethoxylation and/or propoxylation products of alkyl glycosides or linear or branched alcohols containing 12 to 18 carbon atoms in the alkyl moiety and 3 to 20 and preferably 4 to 10 alkyl ether groups. Corresponding ethoxylation and/or propoxylation products of N-alkylamines, vicinal diols, fatty acid esters and fatty acid amides, which correspond to the long-chain alcohol derivatives mentioned in regard to the alkyl moiety, and of alkyl phenols containing 5 to 12 carbon atoms in the alkyl group are also suitable.

Suitable anionic surfactants are, in particular, soaps and anionic surfactants containing sulfate or sulfonate groups with—preferably—alkali metal ions as cations. Preferred soaps are the alkali metal salts of saturated or unsaturated fatty acids containing 12 to 18 carbon atoms. Fatty acids such as these need not even be completely neutralized. Suitable surfactants of the sulfate type include the salts of sulfuric acid semiesters of fatty alcohols containing 12 to 18 carbon atoms and the sulfation products of the above-mentioned nonionic surfactants with low degrees of ethoxylation. Suitable surfactants of the sulfonate type include linear alkyl benzenesulfonates containing 9 to 14 carbon atoms in the alkyl moiety, alkane sulfonates containing 12 to 18 carbon atoms and olefin sulfonates containing 12 to 18 carbon atoms, which are formed in the reaction of corresponding monoolefins with sulfur trioxide, and also α-sulfofatty acid esters which are formed in the sulfonation of fatty acid methyl or ethyl esters.

Surfactants such as these are present in the detergents according to the invention in quantities of, preferably, 5% by weight to 50% by weight and, more preferably, 8% by weight to 30% by weight while the bleaches according to the invention may even be surfactant-free and preferably contain 0.1% by weight to 20% by weight and, more preferably, 0.2% by weight to 5% by weight of surfactants.

A bleach/detergent according to the invention preferably contains at least one water-soluble and/or water-insoluble, organic and/or inorganic builder. Suitable water-soluble organic builders are aminopolycarboxylic acids, more particularly nitrilotriacetic acid and ethylenediamine tetraacetic acid, polyphosphonic acids, more particularly amino-tris-(methylenephosphonic acid), ethylenediamine tetrakis (methylenephosphonic acid) and 1-hydroxyethane-1,1 -diphosphonic acid, polycarboxylic acids, more particularly citric acid and sugar acids, and polymeric (poly)carboxylic acids, more particularly the polycarboxylates of International patent application WO 93/16110 obtainable by oxidation of polysaccharides, polymeric acrylic acids, methacrylic acids, maleic acids and copolymers thereof which may also contain small amounts of polymerizable substances with no carboxylic acid functionality in copolymerized form. The relative molecular weight of the homopolymers of unsaturated carboxylic acids is generally between 5,000 and 200,000 while the relative molecular weight of the copolymers is between 2,000 and 200,000 and preferably between 50,000 and 120,000, based on free acid. A particularly preferred acrylic acid/maleic acid copolymer has a relative molecular weight of 50,000 to 100,000. Suitable, albeit less preferred, compounds of this class are copolymers of acrylic acid or methacrylic acid with vinyl ethers, such as vinyl methyl ethers, vinyl ester, ethylene, propylene and styrene, in which the acid makes up at least 50% by weight. Other suitable water-soluble organic builders are terpolymers which contain two unsaturated acids and/or salts thereof as monomers and vinyl alcohol and/or a vinyl alcohol derivative or a carbohydrate as the third monomer. The first acidic monomer or its salt is derived from a monoethylenically unsaturated $C_{3-8}$ carboxylic acid and preferably from a $C_{3-4}$ monocarboboxylic acid, more particularly (meth)acrylic acid. The second acidic monomer or its salt may be a derivative of a $C_{4-8}$ dicarboxylic acid, maleic acid being particularly preferred. In this case, the third monomeric unit is formed by vinyl alcohol and/or preferably by an esterified vinyl alcohol. Vinyl alcohol derivatives in the form of an ester of short-chain carboxylic acids, for example $C_{1-4}$ carboxylic acids, with vinyl alcohol are particularly preferred. Preferred terpolymers contain 60% by weight to 95% by weight, more particularly 70% by weight to 90% by weight, of (meth)acrylic acid or (meth) acrylate, more preferably acrylic acid or acrylate, and maleic acid or maleate and 5% by weight to 40% by weight and preferably 10% by weight to 30% by weight of vinyl alcohol and/or vinyl acetate. Most particularly preferred terpolymers are those in which the ratio by weight of (meth)acrylic acid or (meth)acrylate to maleic acid or maleate is between 1:1 and 4:1, preferably between 2:1 and 3:1 and more preferably between 2:1 and 2.5:1. Both the quantities and the ratios by weight are based on the acids. The second acidic monomer or its salt may even be a derivative of an allyl sulfonic acid substituted in the 2-position by an alkyl group, preferably by a $C_{1-4}$ alkyl group, or by an aromatic radical preferably derived from benzene or benzene derivatives. Preferred terpolymers contain 40% by weight to 60% by weight and, more particularly, 45% by weight to 55% by weight of (meth)acrylic acid or (meth)acrylate, more especially acrylic acid or acrylate, 10% by weight to 30% by weight and preferably 15% by weight to 25% by weight of methallyl sulfonic acid or methallyl sulfonate and, as the third monomer, 15% by weight to 40% by weight and preferably 20% by weight to 40% by weight of a carbohydrate. This carbohydrate may be, for example, a mono-, di-, oligo- or polysaccharide, mono-, di- or oligosaccharides being preferred. Sucrose is particularly preferred. Predetermined "weak spots" responsible for the ready biodegradability of the polymer are presumably incorporated therein through the use of the third monomer. These terpolymers may be produced in particular by the processes described in German patent DE 42 21 381 and in German patent application DE 43 00 772 and have a relative molecular weight of generally from 1,000 to 200,000, preferably from 200 to 50,000 and more preferably from 3,000 to 10,000. Other preferred copolymers are those described in German patent applications DE 43 03 320 and DE 44 17 734 which preferably contain acrolein and acrylic acid/acrylic acid salts or vinyl acetate as monomers. The organic builders may be used in the form of aqueous solutions, preferably in the form of 30 to 50% by weight aqueous solutions, more particularly for the production of liquid formulations. All the acids mentioned are generally used in the form of their water-soluble salts, more particularly their alkali metal salts.

If desired, the organic builders may be present in bleaches/detergents according to the invention in quantities of up to 40% by weight, preferably in quantities of up to 25% by weight and more preferably in quantities of 1% by weight to 8% by weight. Quantities near the upper limit mentioned are preferably used in paste-form or liquid, more particularly water-containing, bleaches/detergents according to the invention.

Suitable water-soluble inorganic builders are, in particular, polyphosphates, preferably sodium triphosphate. The water-insoluble, water-dispersible inorganic builders used are, in particular, crystalline or amorphous alkali metal alumosilicates which are employed in quantities of up to 50% by weight, preferably in quantities of not more than 40% by weight and, in liquid bleaches/detergents, in quantities of 1% by weight to 5% by weight. Of these, crystalline sodium alumosilicates of detergent quality, more particularly zeolite A, P and optionally X, are preferred. Quantities near the upper limit mentioned are preferably used in solid particulate bleaches/detergents. Suitable alumosilicates have no particles larger than 30 $\mu$m in size, at least 80% by weight preferably consisting of particles less than 10 $\mu$m in size. Their calcium binding capacity, which may be determined in accordance with German patent DE 24 12 837, is generally in the range from 100 to 200 mg CaO per gram.

Suitable substitutes or partial substitutes for the alumosilicate mentioned are crystalline alkali metal silicates which may be present either individually or in admixture with amorphous silicates. The alkali metal silicates suitable for use as builders in the bleaches/detergents according to the invention preferably have a molar ratio of alkali metal oxide to $SiO_2$ of less than 0.95:1 and, more particularly, in the range from 1:1.1 to 1:12 and may be amorphous or crystalline. Preferred alkali metal silicates are sodium silicates, more particularly amorphous sodium silicates with a molar $Na_2O$:$SiO_2$ ratio of 1:2 to 1:2.8. Amorphous alkali metal silicates such as these are commercially available, for example under the name of Portil®. Those with a molar $Na_2O$:$SiO_2$ ratio of 1:1.9 to 1:2.8 may be produced by the process according to European patent application EP 0 425 427. They are preferably added in solid form and not in the form of a solution in the production of the bleaches/detergents according to the invention. Preferred crystalline silicates, which may be present either individually or in admixture with amorphous silicates, are crystalline layer silicates with the general formula $Na_2Si_xO_{2x+1}.yH_2O$, where x—the so-called modulus—is a number of 1.9 to 4 and y is a number of 0 to 20, preferred values for x being 2, 3 or 4. Crystalline layer silicates which correspond to this general formula are described, for example, in European patent application EP 0 164 514. Preferred crystalline layer silicates are those in which x in the general formula mentioned assumes the value 2 or 3. Both β- and δ-sodium disilicates ($Na_2Si_2O_5.yH_2O$) are particularly preferred, β-sodium disilicate being obtainable for example by the process described in International patent application WO 91/08171. δ-Sodium silicates with a modulus of 1.9 to 3.2 may be produced in accordance with Japanese patent applications JP 04/238 809 and JP 04/260 610. Substantially water-free crystalline alkali metal silicates—produced from amorphous alkali metal silicates—with the above-mentioned general formula, in which x is a number of 1.9 to 2.1, obtainable as described in European patent applications EP 0 548 599, EP 0 502 325 and EP 0 452 428, may be used in the bleaches/detergents according to the invention. Another preferred embodiment of the bleaches/detergents according to the invention uses a crystalline sodium layer silicate with a modulus of 2 to 3 obtainable from sand and soda by the process according to European patent application EP 0 436 835. The crystalline sodium silicates with a modulus of 1.9 to 3.5 obtainable by the processes according to European patents EP 0 164 552 and/or EP 0 293 753 are used in another preferred embodiment of the bleaches/detergents according to the invention. If alkali metal alumosilicate, more particularly zeolite, is also present as an additional builder, the ratio by weight of alumosilicate to silicate, based on water-free active substances, is preferably 4:1 to 10:1. In bleaches/detergents containing both amorphous and crystalline alkali metal silicates, the ratio by weight of amorphous alkali metal silicate to crystalline alkali metal silicate is preferably 1:2 to 2:1 and, more particularly, 1:1 to 2:1.

Builders are present in the detergents according to the invention in quantities of up to 60% by weight and more particularly in quantities of 5% by weight to 40% by weight whereas the bleaches according to the invention are preferably free from the builders which merely complex the components of water hardness and preferably contain not more than 20% by weight and, more particularly, from 0.1% by weight to 5% by weight of heavy-metal-complexing agents, preferably from the group consisting of aminopolycarboxylic acids, aminopolyphosphonic acids and hydroxypolyphosphonic acids and water-soluble salts and mixtures thereof.

Enzymes which may be used in addition to the enzymatic bleaching system in the detergents according to the invention are enzymes from the class of proteases, lipases, cutinases, amylases, pullulanases and cellulases and mixtures thereof. Enzymes obtained from fungi or bacteria, such as *Bacillus subtilis, Bacillus licheniformis, Streptomyces griseus, Humicola lanuginosa, Humicola insolens, Pseudomonas pseudoalcaligenes* or *Pseudomonas cepacia* are particularly suitable. The enzymes optionally used and the oxidase to be used in accordance with the invention may be adsorbed onto supports and/or encapsulated in shell-forming materials to protect them against premature inactivation, as described for example in International patent applications WO 92/11347 or WO 94/23005. The additional enzymes mentioned are preferably present in the bleaches/detergents according to the invention in quantities of up to 5% by weight and more particularly in quantities of 0.2% by weight to 2% by weight.

The organic solvents suitable for use in the bleaches/detergents according to the invention, particularly where they are present in liquid or paste-like form, include alcohols containing 1 to 4 carbon atoms, more particularly methanol, ethanol, isopropanol and tert.butanol, diols containing 2 to 4 carbon atoms, more particularly ethylene glycol and propylene glycol, and mixtures thereof and the ethers derivable from the classes of compounds mentioned. Water-miscible solvents of the type in question are present in the bleaches/detergents according to the invention in quantities of preferably not more than 30% by weight and, more particularly, in quantities of 6% by weight to 20% by weight.

To establish a required pH value which is not automatically established by the mixture of other components, the bleaches/detergents according to the invention may contain system-compatible and ecologically safe acids, more particularly citric acid, acetic acid, tartaric acid, malic acid, lactic acid, glycolic acid, succinic acid, glutaric acid and/or adipic acid, and also mineral acids, more particularly sulfuric acid, or bases, more particularly ammonium or alkali metal hydroxides. pH regulators such as these are present in the bleaches/detergents according to the invention in quantities of preferably not more than 20% by weight and, more particularly, in quantities of 1.2% by weight to 17% by weight.

The production of the solid bleaches/detergents according to the invention does not involve any difficulties and, in principle, may be carried out in known manner, for example by spray drying or granulation, the enzymatic bleaching system and any other heat-sensitive substances being added at a later stage. To produce bleaches/detergents according to the invention with a high bulk density, more particularly in the range from 650 g/l to 950 g/l, it is preferred to apply a process comprising an extrusion step as known from European patent EP 486 592. Detergents or bleaches according to the invention in the form of aqueous solutions or other solutions containing typical solvents are produced with particular advantage by simple mixing of the ingredients which may be introduced into an automatic mixer either as such or in the form of a solution.

EXAMPLES

The formation of hydrogen peroxide with the aid of various oxidases was investigated in a buffer system (Davies buffer) and in the presence of an enzyme-, bleach- and bleach-activator-free detergent (concentration 5 g/l) at pH 10/30° C. The $H_2O_2$ concentration was determined photometrically using the Lambert-Beer law via the peroxidase-catalyzed formation of a dye from 4-aminophenazone and chromotropic acid. The concentration of the particular oxidase substrate (D-alanine, choline chloride or glucose) was 25 mmole/l. The oxidases were used in activities of 1 U/ml. In the tests with D-amino acid oxidase and in the comparative tests with glucose oxidase, hydroxylammonium sulfate was additionally present (concentration 1 mmole/l). The hydrogen peroxide concentrations obtained after 30 minutes and 45 minutes are shown in Table 1 below.

TABLE 1

| | Hydrogen peroxide concentration [mmole/l] | | | |
|---|---|---|---|---|
| | Buffer pH 10 | | Detergent, pH 10 | |
| Enzyme | 30 mins. | 45 mins. | 30 mins. | 45 mins. |
| D-amino acid oxidase[a)] | 0.6 | 0.9 | 1.9 | 1.9 |
| Choline oxidase[b)] | 0.5 | 0.7 | 4.0 | 6.5 |
| Glucose oxidase[c)] | 0.06 | 0.1 | 0.3 | 0.3 |

[a)]from pig's kidneys
[b)]from alcaligenes
[c)]from *Aspergillus niger*

Under the typical in-use conditions for detergents, only a slight evolution of hydrogen peroxide could be measured where the glucose-oxidase/glucose system was used as opposed to the systems according to the invention.

What is claimed is:

1. A bleaching detergent composition comprising:

a) an enzymatic bleaching system that produces hydrogen peroxide under aqueous conditions comprising an enzyme having amino alcohol oxidase activity and a substrate for said enzyme;

b) a bleach activator; and c) a linear alkyl benzene sulfonate surfactant.

2. A composition according to claim 1, wherein the enzymatic bleaching system comprises choline oxidase and choline.

3. A composition according to claim 2 having an oxidase activity of 30 U/g to 20,000 U/g.

4. A composition according to claim 3, said composition being in free-flowing particle form and having a bulk density of 300 g/l to 1200 g/l.

5. A composition according to claim 4 having a bulk density of 500 g/l to 900 g/l.

6. A composition according to claim 2 having a liquid or paste form.

7. A composition according to claim 6 having a non-aqueous liquid or paste form.

8. A composition according to claim 6 in the form of an aqueous liquid or paste in a hermetically sealed container.

9. A composition according to claim 1, wherein the enzyme or the substrate are encapsulated in a substance that is impermeable to the enzyme or substrate at room temperature.

10. A method of bleaching fabric stains comprising contacting a fabric in need thereof with an effective amount of an enzymatic bleaching system comprising an enzyme having amino alcohol oxidase activity and a substrate for said enzyme in the presence of a linear alkyl benzene sulfonate surfactant.

11. A method of reducing dye transfer in a wash liquor from a dyed fabric to an undyed or differently colored fabric comprising providing said wash liquor with an effective amount of an enzyme having amino alcohol oxidase activity and a substrate for said enzyme in the presence of a linear alkyl benzene sulfonate surfactant.

* * * * *

UNITED STATES PATENT AND TRADEMARK OFFICE

CERTIFICATE OF CORRECTION

PATENT NO. : 6,409,770 B1
DATED : June 25, 2002
INVENTOR(S) : Weiss et al.

It is certified that error appears in the above-identified patent and that said Letters Patent is hereby corrected as shown below:

Title page,
Item [75], Inventors, delete "Maria", and insert -- Marita --.

Column 10,
Line 67, after "surfactant", insert -- and a bleach activator --.

Column 12,
Line 2, after "surfactant", insert -- and a bleach activator --.

Signed and Sealed this

Ninth Day of September, 2003

JAMES E. ROGAN
*Director of the United States Patent and Trademark Office*